US 6,804,551 B2

(12) United States Patent
Griffin et al.

(10) Patent No.: US 6,804,551 B2
(45) Date of Patent: Oct. 12, 2004

(54) METHOD AND APPARATUS FOR THE EARLY DIAGNOSIS OF SUBACUTE, POTENTIALLY CATASTROPHIC ILLNESS

(75) Inventors: M. Pamela Griffin, Charlottesville, VA (US); J. Randall Moorman, Charlottesville, VA (US); Boris P. Kovatchev, Amherst, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 46 days.

(21) Appl. No.: 09/793,653

(22) Filed: Feb. 27, 2001

(65) Prior Publication Data

US 2002/0052557 A1 May 2, 2002

Related U.S. Application Data

(63) Continuation-in-part of application No. 09/770,653, filed on Jan. 29, 2001, which is a continuation of application No. 09/271,279, filed on Mar. 17, 1999, now Pat. No. 6,216,032.
(60) Provisional application No. 60/078,319, filed on Mar. 17, 1998.

(51) Int. Cl.⁷ ............................................ A61B 5/0456
(52) U.S. Cl. ...................................................... 600/515
(58) Field of Search ................................ 600/372–374, 600/377, 382, 508–509, 513, 515–517, 519, 521

(56) References Cited

U.S. PATENT DOCUMENTS

| | | |
|---|---|---|
| 3,648,688 A | 3/1972 | O'Hanlon, Jr. et al. |
| 3,989,034 A | 11/1976 | Hojaiban |
| 4,018,219 A | 4/1977 | Hojaiban |
| 4,510,944 A | 4/1985 | Porges |
| 4,832,038 A | 5/1989 | Arai et al. |
| 4,862,361 A | * 8/1989 | Gordon et al. ......... 364/413.06 |
| 4,905,706 A | 3/1990 | Duff et al. |
| 5,191,524 A | 3/1993 | Pincus et al. |
| 5,509,425 A | 4/1996 | Feng |
| 5,562,596 A | 10/1996 | Pincus et al. |
| 5,649,544 A | 7/1997 | Feng |

(List continued on next page.)

OTHER PUBLICATIONS

J.S. Richman et al.: "Physiological Time–Series Analysis Using Approximate Entropy and Sample Entropy", Am. J. Physiology Heart Circ. Physio.. 278: H2039–H2049, 2000.*

(List continued on next page.)

*Primary Examiner*—Jeffrey R. Jastrzab
*Assistant Examiner*—Frances P. Oropeza
(74) *Attorney, Agent, or Firm*—Robert J. Decker

(57) ABSTRACT

In one aspect of the invention, there is provided a method and apparatus for early detection of subacute, potentially catastrophic illness in a patient. The method comprises: (a) monitoring heart rate variability in the patient; and (b) identifying at least one characteristic abnormality in the heart rate variability that is associated with the illness. This method can be use to diagnose illnesses such as, but not limited to, sepsis, necrotizing enterocolitis, pneumonia and meningitis, as well as noninfectious illnesses. In another aspect of the present invention, there is provided a method and apparatus for early detection of subacute, potentially catastrophic illness in a patient. The method comprises: (a) monitoring the patient's RR intervals; (b) generating a normalized data set of the RR intervals; (c) calculating one or more of (i) moments of the data set selected from the second and higher moments, including the standard deviation (ii) percentile values of the data set, (iii) sample entropy, and (iv) sample asymmetry; and (d) identifying an abnormal heart rate variability associated with the illness based on one or more of the moments, the percentile values, sample entropy, and sample asymmetry analysis.

23 Claims, 8 Drawing Sheets

U.S. PATENT DOCUMENTS

| | | | |
|---|---|---|---|
| 5,724,983 A | 3/1998 | Selker et al. | |
| 5,749,900 A | 5/1998 | Schroeppel et al. | |
| 5,769,793 A | 6/1998 | Pincus et al. | |
| 5,846,189 A | 12/1998 | Pincus et al. | |
| 6,217,525 B1 * | 4/2001 | Medema et al. | 600/508 |

OTHER PUBLICATIONS

John C. Nelson, et al.: "Probing The Order Within Neonatal Heart Rate Variability", Pediatric Research, vol. 43, No. 6, pp. 823–831 (1998).

Paul J. Godin, et al.: "Experimental Human Endotoxemia Increases Cardiac Regularity: Results From A Prospective, Randomized Crossover Trial", Critical Care Medicine, vol. 24, No. 7 (1996).

Clark E. Allen, et al.: "Nonlinearity Of Heart Rate In The Neonate", American Journal of Perinatology, vol. 12, No. 2, pp. 116–121 (Mar. 1995).

Ali A. Aghili, et al.: "Scaling And Ordering Of Neonatal Heart Rate Variability", Physical Review Letters, vol. 74, No. 7, pp. 1254–1257 (Feb. 13, 1995).

Viola Prietsch, et al.: "Continuous Monitoring Of Heart Rate Variability In Preterm Infants", Early Human Development, vol. 37, No. 2, pp. 117–131 (May 1994).

M. Pamela Griffin, et al.: "The Dynamic Range Of Neonatal Heart Rate Variability",Journal of Cardiovascular Electrophysiology, Vo. 5, No. 2, pp. 112–124 (Feb. 1994).

J.S. Richman, et al.: "Physiological Time–Series Analysis Using Approximate Entropy and Sample Entropy," Am. J. Physiology Heart Circ. Physiol. 278: H2039–H2049, 2000.

Manuscript of M. Pamela Griffin, et al.: "Toward the Early Diagnosis of Neonatal Sepsis and Sepsis–Like Illness Using Novel Heart Rate Analysis," Pediatrics.

C. Van Ravenswaaij–Arts et al.: "Spectral Analysis Of Heart Rate Variability in Spontaneously Breathing Very Preterm Infants", ACTA Pediatr 83: 473–80 (1994).

V. L. Schechtman, et al.: "Development Of Heart Rate Dynamics During Sleep–Waking States In Normal Infants", Pediatric Research, vol. 34, No. 2, pp. 618–623 (1993).

Christopher S. Garrard, et al.: "Spectral Analysis Of Heart Rate Variability In The Sepsis Syndrome", Clinical Autonomic Research, Vo. 3, pp. 5–13 (1993).

Conny M. A. Van Ravenswaaij–Arts, et al.: "The Influence Of Respiratory Distress Syndrome On Heart Rate Variability In Very Preterm Infants", Early Human Development, vol. 27, No. 3, pp. 207–221 (Dec. 1991).

Marc Boucher, et al.: Perinatal Listeriosis (Early–Onset): Correlation Of Antenatal Manifestations And Neonatal Outcome, Obstetrics and Gynecology, vol. 68, No. 5, pp. 593–597 (Nov. 1986).

Ronald D. Berger, et al.: "An Efficient Algorithm For Spectral Analysis Of Heart Rate Variability", IEEE Transactions on Biomedical Engineering, vol. BME–33, No. 9, pp. 900–904 (Sep. 1986).

Patricia Braly, et al.: "Fetal Heart Rate Patterns In Infants In Whom Necrotizing Enterocolitis Develops", Archieves of Surgery, American Medical Association Publication, vol. 115, pp. 1050–1053 (Jan.–Dec. 1980).

Luis A. Cabal, et al.: "Factors Affecting Heart Rate Variability In Preterm Infants", Pediatrics, vol. 65, No. 1, pp. 50–56 (Jan. 1, 1980).

Arnold J. Rudolph, et al.: "Cardiodynamic Studies In The Newborn", Pediatrics, vol. 36, No. 4, pp. 551–559 (Oct. 1965).

* cited by examiner

METHOD AND APPARATUS FOR THE EARLY DIAGNOSIS OF SUBACUTE, POTENTIALLY CATASTROPHIC ILLNESS

CROSS-REFERENCE TO RELATED APPLICATIONS

This application is a Continuation-In Part Application of U.S. patent application Ser. No. 09/770,653 (filed Jan. 29, 2001), which is a Continuation Application of U.S. patent application Ser. No. 09/271,279 (filed Mar. 17, 1999) (now U.S. Pat. No. 6,216,032B1), which claims priority under 35 U.S.C. §119(e) of Provisional Application No. 60/078,319 (filed Mar. 17, 1998), which applications are incorporated herein in their entireties.

FIELD OF THE INVENTION

The present invention relates to the indication of early phases of potentially catastrophic illnesses and relates to heart rate variability monitoring in patients. In particular, the present invention relates to methods and apparatus for early detection of potentially catastrophic illnesses in a patient.

BACKGROUND OF THE INVENTION

Approximately 40,000 very low birth weight ("VLBW") infants (less than 1,500 gm) are born in the United States each year. Ventura et al., "Advance Report of Final Natality Statistics, 1994," *Monthly Vital Statistics Report;* 44, pp. 1–88 (1996). Survival of this group has improved with advances in neonatal intensive care, but late-onset sepsis and necrotizing enterocolitis ("NEC") continue to be major causes of morbidity and mortality. Stoll B. J., Gordon T., Korones S. B., Shankaran S., Tyson J. E., Bauer C. R., "Late-onset Sepsis in Very Low Birth Weight Neonates: A Report from the National Institute of Child Health and Human Development Neonatal Research Network," *Journal of Pediatrics;* 129:63–71 (1996); Gray J. E., Richardson D. K., McCormick M. C., Goldmann D. A., "Coagulase-Negative Staphylococcal Bacteremia Among Very Low Birth Weight Infants: Relation to Admission Illness Severity, Resource Use, and Outcome," *Pediatrics,* 95:225–230 (1995). Unfortunately these illnesses are common in neonates, and infected infants have a significant increase in the number of days spent on the ventilator and an average increase in duration of hospital stay of 25 days. See Stoll et al. above.

Neonatal sepsis occurs in as many as 25% of infants weighing less than 1,500 gm at birth, and the rate is about 1 per 100 patient days. Gladstone, I. M., R. A. Ehrenkrantz, S. C. Edberg, and R. S. Baltimore, "A Ten-Year Review of Neonatal Sepsis and Comparison with the Previous Fifty Year Experience," *Pediatric Infectious Disease Journal;* 9:819–825 (1990); Moro, M. L., A. DeToni, I. Stolfi, M. P. Carrieri, M. Braga, and C. Zunin, "Risk Factors for Nosocomial Sepsis in Newborn Infants and Intermediate Care Units," *European Journal of Pediatrics;* 155:315–322 (1996). The National Institute of Child Health & Human Development ("NICHD") Neonatal Research Network found that neonates who develop late-onset sepsis have a 17% mortality rate, more than twice the 7% mortality rate of noninfected infants.

Risk factors for late-onset sepsis are ubiquitous in the neonatal intensive care unit ("NICU"): intubation, umbilical catheters, prolonged mechanical ventilation, low birth weight, parenteral nutrition via central venous catheters, respiratory distress syndrome, bronchopulmonary dysplasia, severe intraventricular hemorrhage, and nasogastric and tracheal cannulae are all independently associated with sepsis. See Moro et al. supra. Each interventional device represents a potential source of infection and increases the risk of catastrophic infectious illness. Id.

Necrotizing enterocolitis affects up to 4,000 infants in the U.S. yearly, and an estimated 10 to 50% of infants who develop NEC die. Neu, J., "Necrotizing Enterocolitis," *Pediatric Clinics of North America* 43:409–432 (1996). Infants who develop NEC often require intubation and an increase in respiratory support. Survivors are often left with strictures and short-bowel syndrome.

Unfortunately, prior to the discovery of the present invention there has been no reliable clinical means for early diagnosis of these diseases. Clinical neonatologists caring for these VLBW infants recognize sepsis and NEC as potentially catastrophic illnesses, and thus do not hesitate to obtain blood cultures and administer antibiotics empirically at the first appearance of symptoms in an attempt to avert disaster. Likewise, physicians do not hesitate to stop feeding and obtain radiographic studies should any abdominal finding occur. Early diagnosis of neonatal sepsis is difficult (Escobar, G. J, "The Neonatal "Sepsis Work-up": Personal Reflections on the Development of an Evidence-Based Approach Toward Newborn Infections in a Managed Care Organization," *Pediatrics,* 103:360–373 (1999)), as the clinical signs are neither uniform nor specific. Because of this, there are many unnecessary blood cultures, many unnecessary administration of short courses of antibiotics to infants without bacterial infection, and many unnecessary interruptions in neonatal nutrition. Moreover, despite these practices, sepsis and necrotizing enterocolitis continue to occur and continue to cause neonatal deaths. Indeed, by the time clinical signs and symptoms for either sepsis or NEC have developed, the illness may have progressed to an irreversible stage.

In addition, not all patients with clinical signs of sepsis have positive blood cultures. While the blood culture is felt to be the gold standard for establishing the diagnosis of sepsis due to systemic bacterial infection, there are concerns regarding its reliability (Kaftan, H. and J. S. Kinney, "Early Onset Neonatal Bacterial Infections," *Seminars in Perinatology,* 22:15–24 (1998)), especially if single samples of small volume are submitted (Aronson, M. D. and D. H. Bor, "Blood Cultures," *Ann. Intern. Med.,* 106:246–253 (1987); Kellogg, J. A., F. L. Ferrentino, M. H. Goodstein, J. Liss, Shapiro, S L, and D. A. Bankert, "Frequency of Low Level Bacteremia in Infants from Birth to Two Months of Age," *Pediatric Infectious Disease Journal,* 16:381–385 (1997)), as is often the practice in critically ill newborn infants. For example, as many as 60% of culture results may be falsely negative if only 0.5 mL blood is obtained from infants with low-colony-count sepsis. Schelonka, R. L., M. K. Chai, B. A. Yoder, D. Hensley, R. M. Brockett, and D. P. Ascher, "Volume of Blood Required to Detect Common Neonatal Pathogens," *J. Pediatr.,* 129:275–278 (1996). In a study of 298 aerobic culture specimens, the mean blood volume submitted was 0.53 mL and 55% of samples contained less than 0.5 mL. Neal, P. R., M. B. Kleiman, J. K. Reynolds, S. D. Allen, J. A. Lemons, and P. L. Yu, "Volume of Blood Submitted for Culture from Neonates," *Journal of Clinical Microbiology,* 24:353–356 (1986). It is suspected that 30–40% of all infants with sepsis have negative blood cultures. For example, in two studies, approximately 20% of infants with infection proven by post-mortem cultures and autopsy were not so identified using pre-mortem blood cultures (Pierce, J. R., G. B. Merenstein, and J. T. Stocker, "Immediate Postmortem Cultures in an Intensive Care Nursery," *Pediatric Infectious Disease,* 3:510–513 (1984); Squire, E., B. Favara, and J. Todd, "Diagnosis of Neonatal Bacterial Infection: Hematologic and Pathologic Findings in Fatal and Nonfatal Cases," *Pediatrics,* 64:60–64 (1970)).

The current hypothesis is that the clinical syndrome of sepsis is brought about by the host response as a response to insults such as bacterial infection. The major host response is the release of cytokines, small circulating peptides that serve as mediators of the inflammatory response. The syndrome common to sepsis and sepsis-like illness has been named the Systemic Inflammatory Response Syndrome (SIRS) (Members of the ACCP/SCCM Consensus Conference Committee, "American College of Chest Physicians/Society of Critical Care Medicine Consensus Conference: Definitions for Sepsis and Organ Failure and Guidelines for the Use of Innovative Therapies in Sepsis," *Critical Care Medicine,* 20:864–874 (1992)), and the pathogenesis suggested to be an imbalance between pro-inflammatory and anti-inflammatory effects of cytokines. Bone, R. C., C. J. Grodzin, and R. A. Balk, "Sepsis: a New Hypothesis for Pathogenesis of the Disease Process," *Chest,* 112:235–243 (1997). In sepsis and sepsis-like illness, circulating cytokines play a major role in initiating and maintaining the inflammatory response, and cytokine levels correlate with the severity of illness. Anderson, M. R. and J. L. Blumer, "Advances in the Therapy for Sepsis in Children," *Pediatric Clinics of North America,* 44:179–205 (1997); Harris, M. C., A. T. J. Costarino, J. S. Sullivan, S. Dulkerian, L. McCawley, L. Corcoran, S. Butler, and L. Kilpatrick, "Cytokine Elevations in Critically Ill Infants with Sepsis and Necrotizing Enterocolitis," *J. Pediatr.,* 124:105–111 (1994); Glauser, M. P., D. Heumann, J. D. Baumgartner, and J. Cohen, "Pathogenesis and Potential Strategies for Prevention and Treatment of Septic Shock: an Update," *Clinical Infectious Diseases,"* 18:S205–S216 (1994). Kuster and colleagues have recently found elevated levels of circulating cytokines for up to two days prior to the clinical diagnosis of clinical sepsis. Kuster, H., M. Weiss, A. E. Willeitner, S. Detlefsen, I. Jeremias, J. Zbojan, R. Geiger, G. Lipowsky, and G. Simbruner, "Interleukin-1 Receptor Antagonist and Interleukin-6 for Early Diagnosis of Neonatal Sepsis 2 Days Before Clinical Manifestation," *Lancet,* 352:1271–1277 (1998). Cytokines have widespread effects on signal transduction processes and may interfere with normal events of Heartrate ("HR") control by the sympathetic and parasympathetic nervous systems. For example, the cytokines TNF-α, IL-1β and IL-6 increase HR, but they blunt HR responses to β-adrenergic agonists. Oddis, C. V. and M. S. Finkel, "Cytokines and Nitric Oxide Synthase Inhibitor as Mediators of Adrenergic Refractoriness in Cardiac Myocytes," *European Journal of Pharmacology,* 320:167–174 (1997); Oddis, C. V., R. L. Simmons, B. G. Hattler, and M. S. Finkel, "Chronotropic Effects of Cytokines and the Nitric Oxide Synthase Inhibitor, L-NMMA, on Cardiac Myocytes," *Biochemical & Biophysical Research Communications,* 205:992–997 (1994). In addition, sepsis and sepsis-like illness are associated with alterations in beta-adrenergic receptor number and distribution, (Tang, C., J. Yang, and M. S. Liu, "Progressive Internalization of Beta-Adrenoceptors in the Rat Liver During Different Phases of Sepsis," *Biochimica et Biophysica Acta,* 1407:225–233 (1998); Hahn, P. Y., P. Yoo, Z. F. Ba, I. H. Chaudry, and P. Wang, "Upregulation of Kupffer Cell Beta-Adrenoceptors and cAMP Levels During the Late Stage of Sepsis," *Biochimica et Biophysica Acta,* 1404:377–384(1998)) and with multiple steps of signal transduction via b-adrenergic receptors. Bernardin, G., A. D. Strosberg, A. Bernard, M. Mattei, and S. Marullo, "Beta-Adrenergic Receptor-Dependent and -Independent Stimulation of Adenylate Cyclase Is Impaired During Severe Sepsis in Humans," *Intensive Care Medicine,* 24:1315–1322 (1998).

Clinicians have found no clinical signs or laboratory test findings to be reliable for very early diagnosis of neonatal sepsis. In fact, 10 to 20 infants are treated for sepsis for every one infant that has a positive blood culture. Gerdes, J. S. and R. A. Polin, "Sepsis Screen in Neonates with Evaluation of Plasma Fibronectin," *Pediatric Infectious Disease Journal,* 6:443–446 (1987). Thus, a successful surveillance strategy which leads to an earlier diagnosis of potentially catastrophic illnesses such as sepsis and NEC as well as non-infectious illnesses in neonates and premature newborns is necessary and critical in decreasing mortality and morbidity. Moreover, such a surveillance strategy is also useful for detecting potentially catastrophic illnesses in other patients, including infants, toddlers, young children, adolescents and adults. The present invention provides such surveillance strategies. Using the novel surveillance strategies of the present invention, the inventors have found that abrupt clinical deteriorations that prompted physicians to obtain blood cultures and start antibiotics were proceeded for up to 24 hours by increasing abnormal heart rate characteristics "HRC" of reduced baseline variability and sub-clinical, short-lived decelerations in HR, and by increasingly abnormal Score for Neonatal Acute Physiology "SNAP" scores.

Heretofore, heart rate variability ("HRV") measurement has been used as a means of assigning long-term prognosis, usually in adults with heart disease. Additionally, since it is known that HRV is abnormal during illness, physicians have traditionally measured HRV as an indication of such illnesses. For example, in healthy newborn infants, time series of heart period (or RR intervals, the time between successive heart beats) show obvious variability. Numerous publications are available which detail the measurement and characterization of such heart rate variability. See, e.g., Ori, Z., G. Monir, J. Weiss, X. Sayhouni, and D. H. Singer, "Heart Rate Variability: Frequency Domain Analysis," *Cardiology Clinics* 10:499–533 (1992); Kleiger, R. E., P. K. Stein, M. S. Bosner, and J. N. Rottman, "Time Domain Measurements of Heart Rate Variability," *Cardiology Clinics* 10:487–498 (1992).

HRV arises from the interplay of the sympathetic and parasympathetic arms of the autonomic nervous system, which act respectively to speed or slow the heart rate. In newborn infants, as in adults, HRV is substantially reduced during severe illness. Burnard, E. D., "Changes in Heart Size in the Dyspnoeic Newborn Infant." *Brit Med J* 1:1495–1500 (1959); Rudolph, A. J., C. Vallbona, and M. M. Desmond, "Cardiodynamic Studies in the Newborn, III. Heart Rate Patterns in Infants with Idiopathic Respiratory Distress Syndrome," *Pediatrics* 36:551–559 (1965); Cabal, L. A., B. Siassi, B. Zanini, J. E. Hodgman, and E. E. Hon, "Factors Affecting Heart Rate Variability in Preterm Infants," *Pediatrics* 65:50–56 (1980); Griffin, M. P., D. F. Scollan, and J. R. Moorman, "The Dynamic Range of Neonatal Heart Rate Variability," *J Cardiovasc. Electrophysiol* 5:112–124 (1994).

These measurements, however, typically involve only a single measurement of HRV and do not include multivariable logistic regression analysis or other mulitvariable predictive statistical models. In addition, these conventional measures of HRV fail to detect abnormal HRV in patients because the measurements, such as standard deviation and power are optimized only to detect low variability. Some types of abnormal HRV patterns do not have low variability and must be detected using other kinds of measures. The present invention overcomes the deficiencies in conventional HRV measurements, and thus is useful as a means of early diagnosis of potentially catastrophic illnesses such as sepsis and necrotizing enterocolitis. These novel measures thus serve to quantify well-established markers of early fetal and neonatal distress, and they add to clinical observations by detecting sub-clinical changes in HRC.

In addition, the new measures have the advantage of reliability in data sets with missed beats, unlike conventional frequency domain measures of heart rate time series. (Bemtson, G. G. and J. R. Stowell, "ECG Artifacts and Heart Period Variability: Don't Miss a Beat," *Psychophysiol*, 35:127–132 (1998).; Schechtman, V. L., K. A. Kluge, and R. M. Harper, "Time Domain System for Assessing Variations in Heart Rate," *Med Biol. Eng. Comp.*, 26:367–373 (1988)).

SUMMARY OF THE INVENTION

Figure 1A:
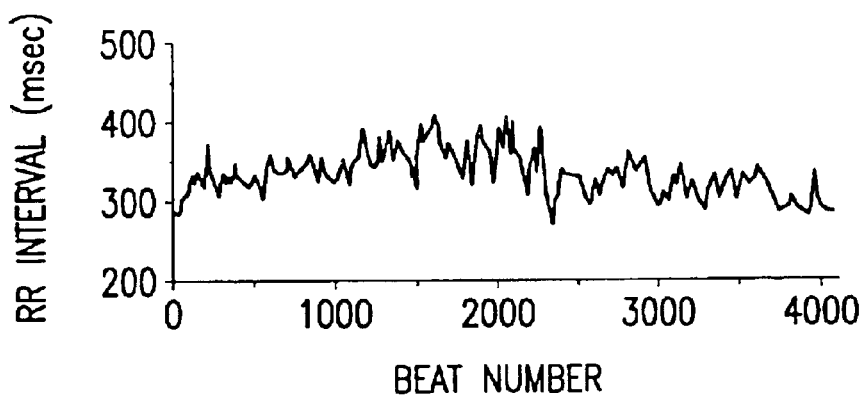
FIGS. 1A to 1C show three 4096 beat RR interval time series. Their corresponding frequency histograms (note the logarithmic ordinate) are shown to the right in FIGS. 1D to 1F. All were recorded from the same infant who had an abrupt clinical deterioration because of coagulase-negative staphylococcal septicemia and an enterococcal urinary tract infection. Panel A shows a normal heart rate time series recorded 6 days before the event. Panels B and C show abnormal heart rate time series recorded within three to six hours before the clinical suspicion of sepsis. The abnormalities are reduced baseline variability and short-lived decelerations of heart rate. A representative deceleration is marked by an arrow in FIG. 1B. The y-axis is RR interval, and the upward spike represents longer RR intervals and thus, a slower rate. The data in FIG. 1C show many such decelerations. These changes lead to asymmetry of the frequency histograms, with positive skewness, that is, there is a longer tail extending toward higher values of RR intervals.

In one aspect of the invention, there is provided a method for early detection of subacute, potentially catastrophic illness in patients. The method comprises: (a) monitoring heart rate variability in the patient; and (b) identifying at least one characteristic abnormality in the heart rate variability that is associated with the illness.

This method can be used to diagnose illnesses such as, but not limited to, sepsis, necrotizing enterocolitis, pneumonia and meningitis, as well as non-infectious illnesses.

Preferably, one or more diagnostic work-ups are conducted for a suspected illness when a characteristic abnormality or abnormalities are identified. Such diagnostic work-ups include, but are not limited to, obtaining blood cultures, taking X-rays, or obtaining pathological specimens from the patient.

In one preferred embodiment, the characteristic abnormality or abnormalities are identified from a normalized data set of RR intervals. A substantially large data set is preferred. Such a data set more preferably contains on the order of about $10^3$ to $10^4$ RR intervals.

The characteristic abnormality or abnormalities are preferably identified based on at least one of the second and higher moments, percentile values (more preferably the $10^{th}$ and $50^{th}$ percentile value), sample entropy, and/or sample asymmetry analysis of the normalized data set.

In another aspect of the present invention, there is provided a method for early detection of subacute, potentially catastrophic illness in a patient. The method comprises: (a) monitoring the patient's RR intervals; (b) generating a normalized data set of the RR intervals; (c) calculating one or more of: (i) moments of the data set selected from the second and higher moment including standard deviation; (ii) percentile values of the data set; (iii) sample entropy; and (iv) sample asymmetry; and (d) identifying an abnormal heart rate variability associated with the illness based on one or more of the moments, percentile values, sample entropy, and sample asymmetry analysis, and correlating the variability to illnesses. The calculation of step (c) is carried out using a multivariable statistical analysis including but not limited to multivariable regression analysis, neural network, k-nearest neighbor analysis, and combinations thereof.

In yet another aspect of the present invention, there is provided an apparatus for early detection of subacute, potentially catastrophic illness in a patient. The apparatus comprises: (a) a monitoring device, monitoring heart rate variability in a patient; and (b) a microprocessor, identifying at least one characteristic abnormality in heart rate variability that is associated with illness. The microprocessor preferably generates a normalized data set of RR intervals and also preferably calculates one or more of the second and higher moments of the data set (more preferably standard deviation, skewness and/or kurtosis), percentile values of the data set (more preferably $10^{th}$ and $50^{th}$ percentile), sample entropy, and/or sample asymmetry analysis of the normalized data set, and identifies the characteristic abnormality based on the same.

Preferably the microprocessor performs steps comprising: (a) generating a normalized data set of the RR intervals; (b) calculating one or more of: (i) moments of the data set selected from the second and higher moments, (ii) percentile values of the data set, (iii) sample entropy; (iv) sample symmetry; (c) identifying an abnormal heart rate variability based on one or more of the moments, the percentile values, sample entropy and sample asymmetry analysis; and (d) correlating the abnormal heart rate variability to said illness.

DETAILED DESCRIPTION OF THE INVENTION

The reasons for reduced HRV during illness has been debated, and three theories concerning the mechanisms of reduced HRV have been developed. These theories focus on the mathematical characteristics of RR interval time series showing normal and low HRV.

The first theory focuses on the notion that the mechanism behind reduced HRV is a reduction of parasympathetic tone. Akselrod, S., D. Gordon, F. A. Ubel, D.C. Shannon, A. C. Barger, and R. J. Cohen, "Power Spectrum Analysis of Heart Rate Fluctuation: a Quantitative Probe of Beat-to-beat Cardiovascular Control," *Science* 213:220–222 (1981); But see Malik, M. and A. J. Camm, "Heart Rate Variability: from Facts to Fancies," *J Am Coll Cardiol* 22:566–568 (1993).

The second theory centers on the notion that normal physiology is more complex than abnormal, hence heart rhythm is more irregular during health. Goldberger, A. L., D. R. Rigney, and B. J. West, "Chaos and Fractals in Human Physiology," *Scientific American* 262:42–46 (1990); Goldberger, A. L., V. Bhargava, B. J. West, and A. J. Mandell, "On a Mechanism of Cardiac Electrical Stability: the Fractal Hypothesis," *Biophys J* 48:525–528 (1985); Goldberger, A. L. and B. J. West "Chaos in Physiology: Health or Disease? Chaos in Biological Systems," H. Degn, A. V. Holden, and L. F. Olsen, editors. Plenum Press, 1–4, New York (1987); Goldberger, A. L. and B. J. West, "Applications of Nonlinear Dynamics to Clinical Cardiology," *Ann NY Acad Sci* 504:195–213 (1987); Goldberger, A. "Fractal Electrodynamics of the Heartbeat In Mathematical Approaches to Cardiac Arrhythmias," J. Jalife, editor, The New York Academy of Sciences, New York. 402–409 (1990); Peng, C.-K., J. Mietus, J. M. Hausdorff, S. Havlin, H. E. Stanley, and A. L. Goldberger, "Long-Range Anticorrelations and Non-Gaussian Behavior of the Heartbeat," *Phys Rev Lett* 70:1343–1346 (1993).

Without wishing to be held to any particular explanation or theory, the present inventors have developed a third theory of the mechanism of observed abnormalities of HRV: an explanation based on the events of signal transduction cascades. See Nelson J. C., Rizwan-Uddin, Griffin M. P., Moorman J. R., "Probing the Order of Neonatal Heart Rate Variability," *Pediatric Research*, 43: 823–831 (1998). The sinus node cell membrane has beta-adrenergic receptors which, on binding agonists released from sympathetic nerve endings or the adrenal medulla, lead to the activation of cAMP-dependent protein kinase, which phosphorylates cardiac ion channels and results in cell depolarization, an action potential, and a heartbeat. This readily explains the rise in heart rate after sympathetic stimulation. The sinus node cell membrane also contains muscarinic acetylcholine receptors—when bound with acetylcholine from parasympathetic nerve endings, the process is inhibited and the heart rate falls. As the amounts of sympathetic and parasympathetic activity vary, so heart rate varies. Thus, for as long as the complex steps of intracellular signal transduction can be successfully completed, the sinus node can be viewed as an amplifier of the input signals of the autonomic nervous system, and heart rate as the output signal.

Consider now a severe illness such as sepsis. In such an unfavorable metabolic milieu, optimal conditions for signal transduction are unlikely. The inventors hypothesized that HRV becomes abnormal during such illness because sinus node cells, like all other cells, are unable to respond normally to sympathetic and parasympathetic inputs. From this viewpoint, sinus node cells report in real time on their ability to respond to adrenergic and muscarinic stimuli. Effective reporting depends on optimal intracellular conditions, and the inventors view HRV as a sensitive measure of the state of cells.

The inventors have found that monitoring HRV in patient populations at high risk leads to an early diagnosis and opportunity for early treatment for potentially catastrophic illnesses, such as severe infections. For example, records of RR intervals in patients prior to the clinical diagnosis of sepsis demonstrate at least two characteristic abnormalities. First, the baseline shows very reduced variability. Second, there are short-lived episodes of deceleration of heart rate. The present invention relates to novel mathematical approaches to detecting these characteristic abnormalities.

The present invention relates to successful patient HRV monitoring, and the ability to distinguish abnormal HRV from normal HRV using objective criteria. Patient HRV correlates with the severity of patient illness such that a decrease in HRV occurs before clinical manifestations of potentially catastrophic illnesses such as sepsis and necrotizing enterocolitis appear.

The invention relates to a real-time heart rate variability monitor whose signal can be interpreted as the probability of an impending catastrophic clinical event. The present invention can be applied in patient populations that are at high risk of potentially catastrophic impending events such as, but not limited to, sepsis, necrotizing enterocolitis, pneumonia and meningitis, as well as non-infectious illnesses. Generally, the method is applicable for diagnosis of illnesses that lead to the systemic inflammatory response syndrome, including sepsis-like illness, a clinical condition in which patients have signs and symptoms of sepsis, but do not have documented infection. The method is also applicable for other sub-acute illnesses that present late in the course with abrupt deterioration, such as intracranial hemorrhage. Patient populations include patients at any life stage, including but not limited to low birth weight infants, premature neonates, newborn infants, infants, toddlers, children, adolescents, and adults.

The invention relates to a process by which monitoring of novel parameters of heart rate variability can be used to make the early diagnosis of subacute illness in patients.

The analysis of the present invention preferably includes all or some of the following steps to construct a digitally filtered and normalized data set from data sets of sufficient numbers of consecutive RR intervals:

1. Acquire EKG signal and RR interval time series data, preferably continuously.

2. Separate into piecewise continuous beat records (e.g., the 4096 beat records used in the Examples).

3. Filter, for example, using a (2M+1) point moving average filter.

$$RR_{(n)} = \frac{1}{2M+1} \sum_{j=-M}^{M} RR_{(n-j)}$$

4. Calculate the mean, variance and standard deviation of each record.

5. Normalize the data by subtracting the mean and dividing by the standard deviation.

6. Calculate, for example, the third and fourth moments of the normalized data, where:

$$m_r = \frac{1}{N} \sum_{j=1}^{N} (X_j - X_{ave})^r$$

where $m_r$, is the rth moment of the time series variable X. The moment coefficient of skewness is $m_3/(m_2)^{3/2}$, and the moment coefficient of kurtosis is $m_4/(m_2)^2$. When the data are normalized, $m_2$ (the variance) is 1, and the third and fourth moments are identical to the skewness and the kurtosis, respectively.

7. Determine percentiles of the normalized filtered data by sorting the intervals from smallest to largest. The 50th percentile value, or P50, is the value halfway from smallest to largest. It is the median value of the data set. In the same way, other percentile values of interest can be determined. For example, P10 is the value that lies 10% of the way between the smallest and the largest. For our data sets of 4096 points, it is the 410th point starting from the smallest.

The present invention also relates to novel parameters of heart rate variability that can be correlated to the presence of potentially catastrophic illness in a patient, which include, but are not limited to, the following:

1. Higher moments of the data, including
   a. The second moment of the digitally filtered and normalized data set (the moment coefficient of standard deviation, also referred to simply as "standard deviation"): a low value signifies abnormally reduced variability, which allows for a diagnosis early in the course of subacute illnesses, such as sepsis.
   b. The third moment of the digitally filtered and normalized data set (the moment coefficient of skewness, also referred to simply as "skewness"): a high positive value indicates the presence of short-lived subclinical decelerations in heart rate, which allows for a diagnosis early in the course of subacute illnesses, such as sepsis.
   c. The fourth moment of the filtered and normalized data set (the moment coefficient of kurtosis, also referred to simply as "kurtosis"): a high positive value indicates a peaked frequency histogram of the RR intervals, which allows for a diagnosis early in the course of subacute illnesses, such as sepsis.
2. Percentiles of the data, such as the 10th percentile value of the filtered and normalized data set (P10): a value closer to 0 allows for a diagnosis early in the course of subacute illnesses, such as sepsis. Other reasonably low percentiles (e.g., P1 to P20) are likely to be equally appropriate. Moreover, characteristic abnormalities of other percentile values (for example, the 25th, 50th (median), 75th and 90th percentile values of data set) are contemplated.
3. Sample entropy (SampEn), which is a measure of relative patterness of data series. SampEn measures complexity and regularity of clinical and experimental time series data. It is the negative logarithm of the conditional probability that two sequences of m+1 points will match within a tolerance r given that they match for the first m points. It is similar to approximate entropy but is significantly less biased, especially for short data series because it does not count sequences as matching themselves. See Richman J. S., Moorman J. R., "Physiological Time-series Analysis Using Approximate Entropy and Sample Entropy," *American Journal of Physiology*, 278: H2039–2049 (2000), which is herein incorporated by reference in its entirety. SampEn is reduced for RR interval records showing reduced variability and transient decelerations.

4. Sample asymmetry analysis is a method of determining asymmetry of frequency histograms. Generally, a power function is used to weigh the deviation of each RR interval in the series from a certain RR interval value. The average weighted deviation for intervals lower than this reference value is calculated, and is lower for RR interval records showing reduced variability and transient decelerations. The average weighted deviation for intervals higher than the median is also calculated, and is higher for RR interval records showing reduced variability and transient decelerations. The ratio right/left weighted deviation is computed as an indicator of asymmetry of each RR sample. For this particular application the power function is assumed quadratic, e.g. the power is 2, and the reference point is the median of each RR sample.

Graphically, the third and fourth moments report on the nature of the frequency histogram of the RR intervals. Specifically, the third moment reports on the symmetry of the histogram, and becomes large as the histogram is skewed to the right by the long RR intervals associated with the episode of relative bradycardia. Since the variance of the normalized record is 1, the third moment is referred to as the skewness. The fourth moment reports on the nature of the peak, and becomes larger as the peak becomes sharper. Since records with predominantly low HRV have RR interval values that are tightly clustered, the histogram has a sharp main peak, and the fourth moment is relatively large. Since the variance of the normalized record is 1, the fourth moment is referred to as the kurtosis. Thus one aspect of the present invention relates to the examination of records for elevated values of skewness and kurtosis.

The present invention also utilizes SampEn, which is a new family of statistics that is related to approximate entropy (ApEn). SampEn was developed to reduce the shortcomings and biases present in ApEn due to the necessity of requiring the counting of self-matches, which suggest more similarity than is actually present. See Richman J. S., Moorman J. R., "Physiological Time-series Analysis Using Approximate Entropy and Sample Entropy," *American Journal of Physiology*, 278: H2039–2049 (2000). SampEn (m, r, N) is precisely the negative natural logarithm of the conditional probability that two sequences similar for m points remain similar at the next point, where self-matches are not included in calculating the probability. Thus, a lower value of SampEn also indicates more self-similarity in the time series.

In addition to eliminating self-matches and the inherent bias, the SampEn algorithm is simpler than the ApEn algorithm, requiring approximately one-half as much time to calculate. Further, SampEn is largely independent of record length and displays relative consistency under circumstances where ApEn does not. Further, SampEn does not use a template-wise approach when estimating conditional probabilities. To be defined, SampEn requires only that one template find a match of length m+1. SampEn does not consider self-matches. Second, only the first N−m vectors of length m are considered, which ensures that, for $1 \leq i \leq N-m$, $\chi_{m(i)}$ and $x_m+1^{(i)}$ $\omega_{m+1(i)}$ are defined.

We defined $B_i^m(r)$ as $(N-m-1)^{-1}$ times the number of vectors $x_m(j)$ within r of $x_m(i)$, where j ranges from 1 to N−m, and $j \neq i$ to exclude self-matches. We then defined $B^m(r) = (N-m)^{-1} \Sigma_{i=1}^{N-m} B_i^m(r)$. Similarly we defined $A_i^m(r)$ as $(N-m-1)^{-1}$ times the number of vectors $x_{m+1}(j)$ within r of $x_{m+1}(i)$, where j ranges from 1 to N−m($j \neq i$), and set $A^m(r) = (N-m)^{-1} \Sigma_{i=1}^{N-m} A_i^m(r)$. $B^m(r)$ is then the probability that two sequences will match for m points, whereas $A^m(r)$ is the probability that two sequences will match for m+1 points. We then defined the parameter SampEn(m, r)=$\lim_N \to \infty \{-1 \ln [A^m(r)/B^m(r)]\}$, which is estimated by the statistic SampEn(m, r, N)=$-1 \ln [A^m(r)/B^m(r)]$. Where there is no confusion about the parameter r and length m of the template vector, we set $B = \{[(N-m-1)(N-m)]/2\} B^m(r)$ and $A = \{[(N-m-1)(N-m)]/2\} A^m(r)$, so that B is the total number of template matches of length m and A is the total number of forward matches of length m+1. We note that $A/B = [A^m(r)]/B^m(r)]$, so SampEn(m, r, N) can be expressed as $-1 \ln (A/B)$.

The quantity A/B is precisely the conditional probability that two sequences within a tolerance r for m points remain within r of each other at the next point. In contrast to ApEn(m, r, N), which calculates probabilities in a template-wise fashion, SampEn(m, r, N) calculates the negative logarithm of a probability associated with the time series as a whole. SampEn(m, r, N) will be defined except when B=0, in which case no regularity has been detected, or when A=0, which corresponds to a conditional probability of 0, and in infinite value of SampEn(m, r, N). The lowest nonzero conditional probability that this algorithm can report is $2[(N-m-1)(N-m)]^{-1}$. Thus, the statistic SampEn(m, r, N) has in (N−m)+1ln(N−m−1)−1n(2) as an upper bound, nearly doubling in (N−m), the dynamic range of ApEn(m, r, N).

The present invention also utilizes Sample Asymmetry analysis of RR intervals. This analysis includes weighting of all RR intervals with respect to their deviation from a reference point, followed by computation of left weighted deviation ($R_1$), right weighted deviation ($R_2$) and their ratio $R=R_2/R_1$, which is the defined here sample asymmetry. The definition of sample asymmetry follows the following formal mathematical construction:

a) Defining weighting power function: Let $\xi$ be a random variable with values in its sampling space X and unspecified distribution, and let $\mu \in X$ be a point within the sampling space X. For any $x \in X$ we define a weighting function $w(x; \alpha) = (x-\mu)^\alpha$, where $\alpha > 0$ is a parameter describing the degree of weighting of deviations from the reference point $\mu$. For example, if $\alpha = 1$, deviations from $\mu$ will receive linearly increasing weights, while if $\alpha = 2$, deviations from $\mu$ will receive quadratically increasing weights. Note that the weighting parameter $\alpha$ could be selected in various applications to be any positive, including non-integer, number. A number smaller than 1 will result in slower than linear increase of weights, a number greater than 2 will result in a faster than quadratic increase of weights.

In order to add flexibility to this model, a different degree of weighting to the left ($\alpha$) and to the right ($\beta$) from the reference point $\mu$ can be employed. In many applications the left- and right weightings could be equal. Separate weightings for left and right deviations of from its reference point $\xi$ are defined as follows:

Left weighting function: $w_1(x; \alpha) = w(x; \alpha)$ whenever $x < \mu$ and 0 otherwise;

Right weighting function: $w_1(x; \beta) = w(x; \beta)$ whenever $x \geq \mu$ and 0 otherwise, where the parameters, similarly to a, describes the degree of weighting of deviation to the right of the reference point.

b) Defining Sample Asymmetry of a random variable: Let $x_1, x_2, \ldots x_n$ be a sample of n observations on $\xi$. Given this sample, two quantities representing the sum of the weighted deviations to the left and to the right from the reference point $\mu$ are defined as follows:

$$R_1(\alpha) = \frac{1}{n} \sum_{i=1}^{n} w_1(x_i; \alpha) \text{ and}$$

$$R_2(\beta) = \frac{1}{n} \sum_{i=1}^{n} w_1(x_i; \beta) \text{ respectively.}$$

Thus, if $\alpha = \beta$, and the sample $x_1, x_2, \ldots x$ is approximately symmetric with respect to the reference point, then $R_1$ will be approximately equal to $R_2$. If the sample is asymmetric with larger, and/or more frequent deviations to the right from the reference point $\mu$, then $R_2$ will be greater than $R_1$. Inversely, if the sample is asymmetric with larger, and/or more frequent deviations to the left from the reference point $\mu$, then $R_1$ will be greater than $R_2$.

The ratio $R(\alpha, \beta) = R_1(\alpha)/R_2(\beta)$ represents the sample asymmetry of the random variable $\xi$.

The following properties are pertinent to this application of sample asymmetry:

If $\alpha = \beta$, when the sample $x_1, x_2, \ldots x_n$ is approximately symmetric with respect to the reference point, then $R(\alpha, \beta)$ will be approximately equal to 1. Values greater than one will indicate larger, and/or more frequent deviations to the right from the reference point $\mu$ while values less than one will indicate larger, and/or more frequent deviations to the left.

The sensitivity of the ratio $R(\alpha, \beta)$ to left- and right deviations from the reference point can be controlled through separate adjustment of the parameters $\alpha$ and $\beta$.

$R_1(\alpha)$ and $R_2(\beta)$ can be used separately as estimates of the absolute weighted mass of the distribution of 4 with respect to its reference point $\mu$.

The reference point u can be the empirical mean of the random variable $\xi$, e.g., $$\bar{x} = \frac{1}{n} \sum_{i=1}^{n} x_i,$$

the median of $\xi$, or any other theoretically, or practically relevant number.

If $\mu$ is the mean (or the median) of the distribution and $\alpha = \beta = 2$ then, under the null hypothesis that the distribution is normal, the sample asymmetry R(2,2) will have an F-distribution with (n/2−1;n/2−1) degrees of freedom (n/2−1/2;n/2−3/2 if n is odd number). This property gives a straightforward test for symmetry of a single data sample.

Abnormalities in HRV that are characteristic of illness can be identified, for example, by comparing the above parameters of heart rate variability to threshold or by combining multiple measurements of HRV using logistic regression models, neural networks, multiple variable analysis, nearest neighbor analysis, or other predictive mathematical instruments. Appropriate parameters for thresholds or for mathematical modeling can be assigned by those skilled in the art. Ideally, these parameters will be based on the results of a large group of patients, for example, a group of newborn patients at risk of sepsis and necrotizing enterocolitis. For example, from the infants observed to date, reasonable threshold values include: skewness on the order of about 1 or more, kurtosis on the order of about 7 or more and P10 on the order of about −1.1 or more.

EXAMPLES

Example 1

Study Population

Infants who had risk factors for acquiring late-onset sepsis were monitored in the neonatal intensive care unit at the University of Virginia from August 1995 to April 1999. These risk factors included low birth weight, prematurity, need for central venous access, and NICU stay longer than 2 weeks. Three groups of infants defined by the actions of the physicians and the results of blood cultures were studied. Infants who had an abrupt clinical deterioration after 3 days of age that prompted physicians to obtain blood cultures and to give antibiotics were in the sepsis (positive blood culture) or sepsis-like illness (negative blood culture) group. The infants without sepsis group raised no clinical suspicion of sepsis and had no blood cultures obtained over a 10-day period. HRC monitoring results were not visible to the treating physicians and did not influence medical management.

Heart Rate Data Acquisition and Analysis

An analog EKG voltage signal from the bedside monitor (Marquette) was digitized and filtered, and then evaluated for QRS complexes using specially-equipped PCs (National Instruments AT-DSP2200). RR intervals were compared with the previous 100 intervals and excluded if they differed by more than 5 S.D. All data sets were visually inspected, and records with obviously artefactual data were excluded. This resulted in removal of 1% of all the data sets. HRC measures were calculated from 4096-beat epochs of RR intervals.

HRC Analysis

HRC measures that give a description of the symmetry of the histogram of RR intervals were selected. "Moments" are descriptive statistics calculated from the individual differences of data points from the mean. The first moment is itself the mean and the second moment is the standard deviation, the square root of the average of the squared individual differences. The third moment or skewness reports on the symmetry of the histogram. A symmetrical histogram has a skewness of 0, and a histogram with a tail of values that are larger than the median has positive skewness. Weisstein, E. W., "CRC Concise Encyclopedia of Mathematics," Chapman and Hall/CRC, Boca Raton (1999). "Percentiles" of the data were also calculated. The median is the $50^{th}$ percentile data point, meaning that it resides at the mid-point of the data after sorting from smallest to largest. In addition to the median, the p50, the p10 (10th percentile data point), p25 (25th percentile data point), p75 (75th percentile data point) and p90 (90th percentile data point) were calculated. Prior to these calculations, the mean and S.D. were used to normalize the data so that the mean and S.D. of each 4096-beat record were 0 and 1 respectively. This normalization allowed direct comparison of HRC among all records. It is important to note that these measures are based only on the distribution of the data points and not the sequence in which they occur. These measures are not changed by missing points, unlike frequency domain measures. Berntson, G. G. and J. R. Stowell, "ECG artifacts and heart period variability: don't miss a beat," *Psychophysiol*, 35:127–132 (1998).

Clinical Scores

The SNAP (Richardson, D. K., J. E. Gray, M. C. McCormick, K. Workman, and D. A. Goldmann, "Score for Neonatal Acute Physiology: a physiologic severity index for neonatal intensive care," *Pediatrics*, 91:617–623 (1993)) and NTISS (Gray, J. E., D. K. Richardson, M. C. McCormick, K. Workman-Daniels, and D. A. Goldmann, "Neonatal therapeutic intervention scoring system: a therapy-based severity of illness index," *Pediatrics*, 90:561–567 (1992)) scores were obtained either prospectively or from chart review by trained research assistants who were closely supervised. Scores were calculated for 24-hour epochs relative to the time that the suspicion of sepsis was raised. The investigators were blinded to the results of the HRC analysis at the time of scoring.

Strategy

To examine the time course of HRC early in sepsis, the time period of five days before and three days after a reference time point were analyzed. For this, time that was used was either the time at which the blood culture was obtained (sepsis and sepsis-like illness groups) or a random time (infants without sepsis). The event time for infants without sepsis was assigned randomly during the 6th or $_7$th day of their 10-day course. The data in 6-hour epochs based on this reference point were analyzed. HRC for all the 4096-beat data sets was calculated, and each 6-hour epoch as the median value of each measure for each patient was summarized. Epochs with less than 50% of the expected number of heartbeats was excluded. For comparison with clinical illness severity scores in the regression analysis, HRC in 24-hour epochs were analyzed and compared with the results with clinical scores obtained over the same period.

Statistical Analysis

The significance of differences in demographic characteristics and HRC for isolated time points was examined using the Mann-Whitney rank sum test or ANOVA (SigmaStat, Jandel). The significance of differences between groups for the 24 hours before and after the event were analyzed using ANOVA with a Tukey test for multiple comparisons (SigmaStat, Jandel). ROC analysis was performed using Microsoft Excel and the Analyze-it plug-in (Analyze-it Software). Multivariable logistic regression analysis was used to examine the ability of HRC and clinical scores to distinguish septic infants from infants without sepsis (S-Plus).

Table I shows the demographic characteristics of the infants studied. There were 46 culture-proven episodes of sepsis in 40 patients. There were 2 deaths associated with *Staphylococcus aureus* and Enterococcus infection. The most common organisms isolated were coagulase-negative Staphylococcus (n=20) and Staphylococcus aureus (n=15). There were 27 episodes of culture-negative sepsis in 23 infants. In the control group, there were 29 control periods in 26 patients. In the culture-positive sepsis group, the mean (S.D.) birth weight, gestational age and post-conceptional age at event were 784 g (409), 26 weeks (2), and 31 weeks (4). In the culture-negative sepsis-like illness group, the values were 756 g (258), 26 weeks (2) and 30 weeks (3). In the infants without sepsis, the values were 976 g (265), 28 weeks (3), and 33 weeks (3). For each parameter, the values for the control group were significantly higher than for the sepsis and sepsis-like illness groups (p<0.001), but the sepsis group was not significantly different from the sepsis-like illness group.

Heart Rate Analysis

Figure 1B:
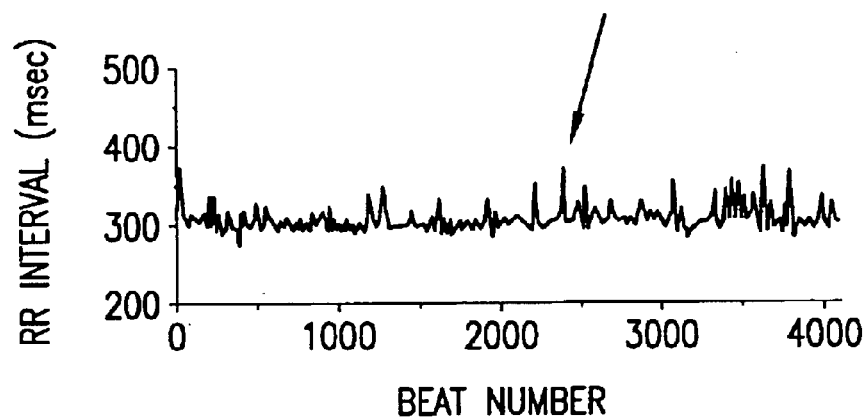
Figure 1C:
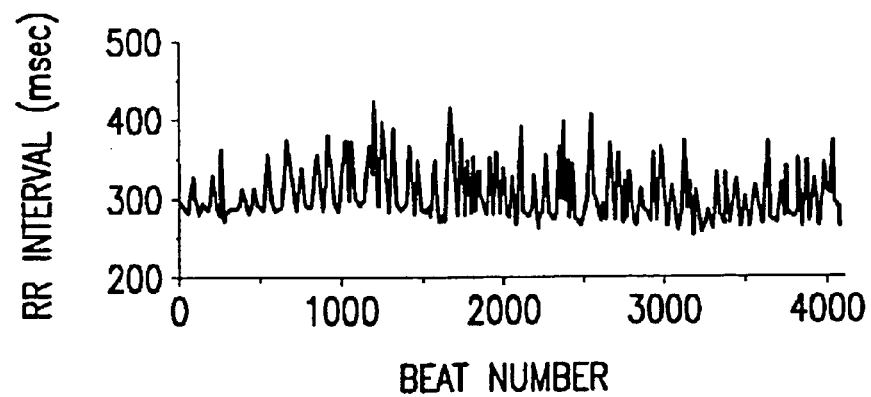
Figure 1D:
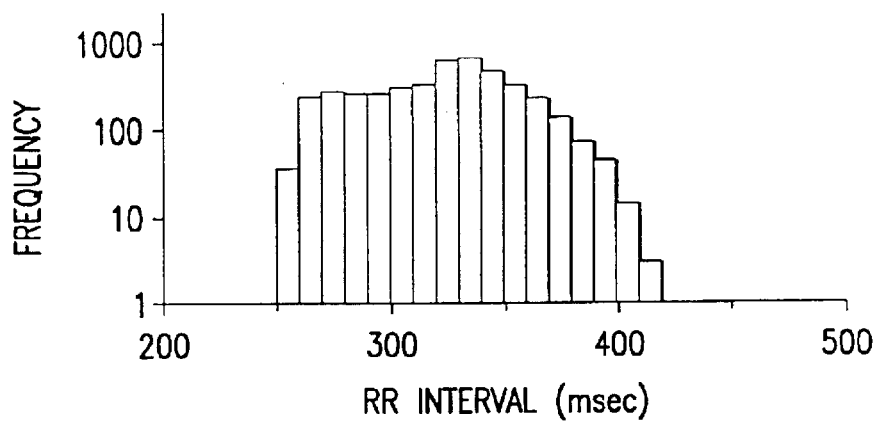
FIG. 1 illustrates an exemplary Heart Rate Characteristic ("HRC") analysis.
Figure 1E:
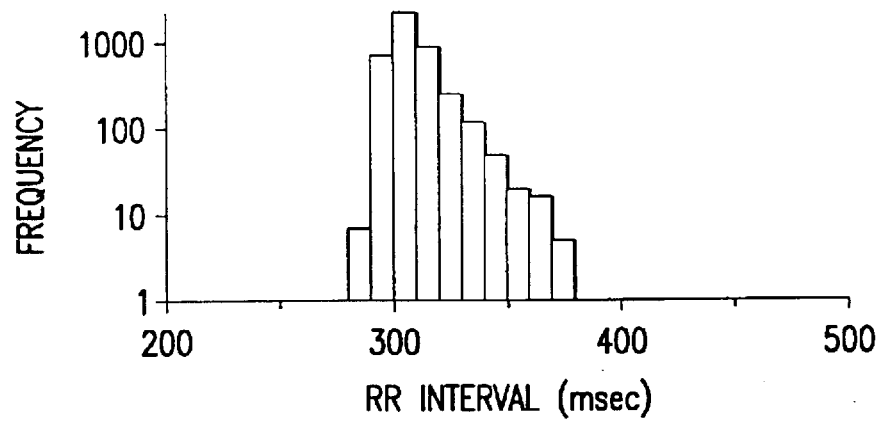
Figure 1F:
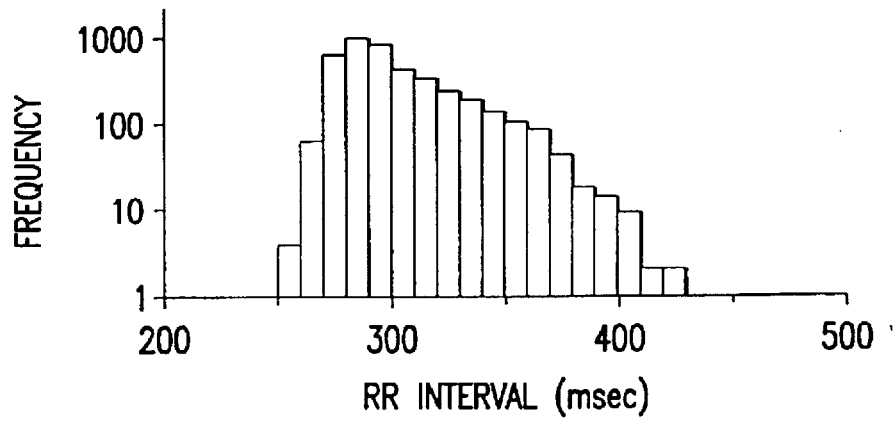
Figure 2B:
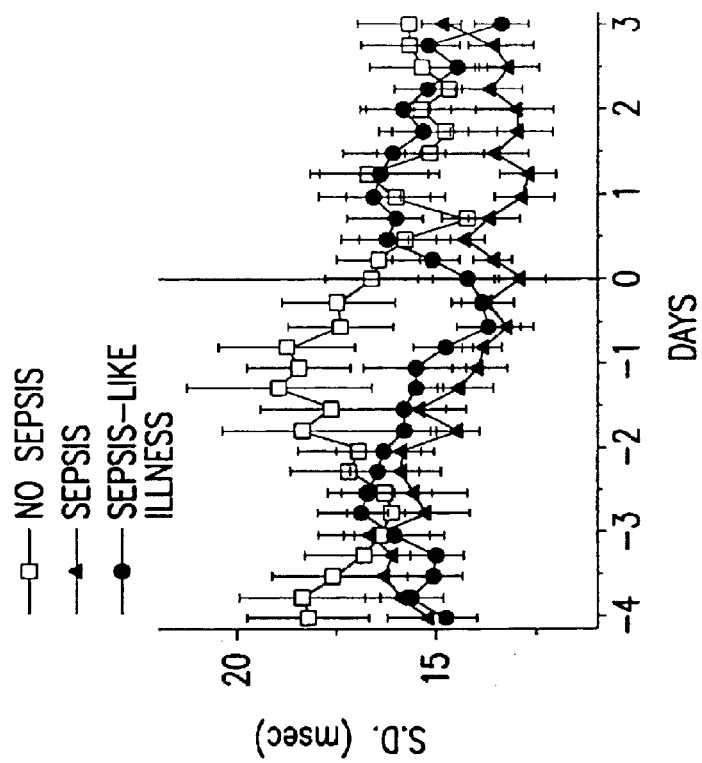
FIG. 2 depicts the results of a time course of HRC measures. Data points summarize a six-hour epoch ending at the time value on the abscissa. Day 0, which ends at the time of the abrupt clinical deterioration, is marked with a vertical line and the word CRASH (Cultures, Resuscitation and Antibiotics Started Here). Bars are standard error of the mean. Panel A depicts the mean RR interval. Panel B depicts standard deviation (S.D.). As can be seen, there are no significant differences in the mean RR interval and standard deviation (A and B). Panel C depicts skewness and panel D depicts the $50^{th}$ percentile data point, or the median (p50). The novel HRC measures skewness and p50 change over the 24 hours before the event in the sepsis and sepsis-like illness groups as shown in Panels C and D.
Figure 2A:
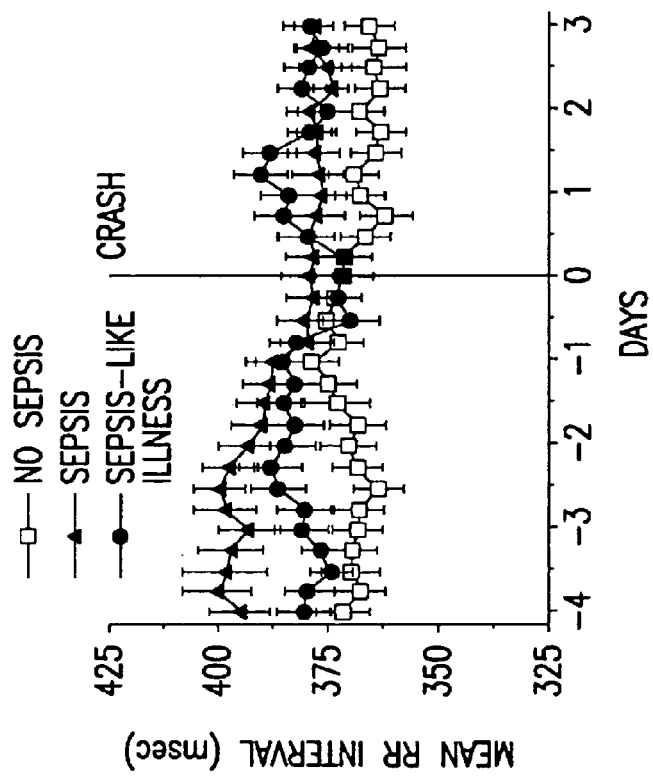
Figure 2D:
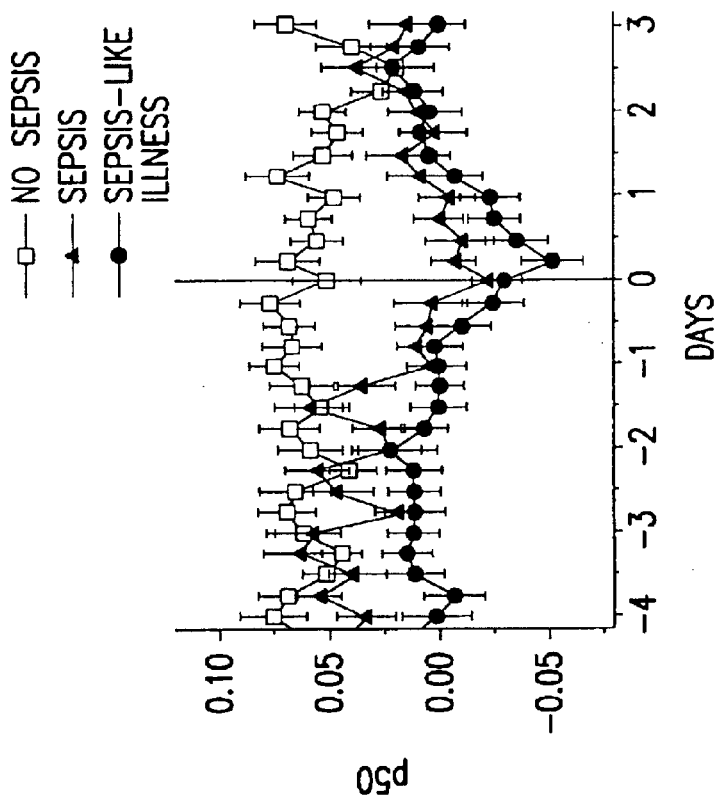
Figure 2C:
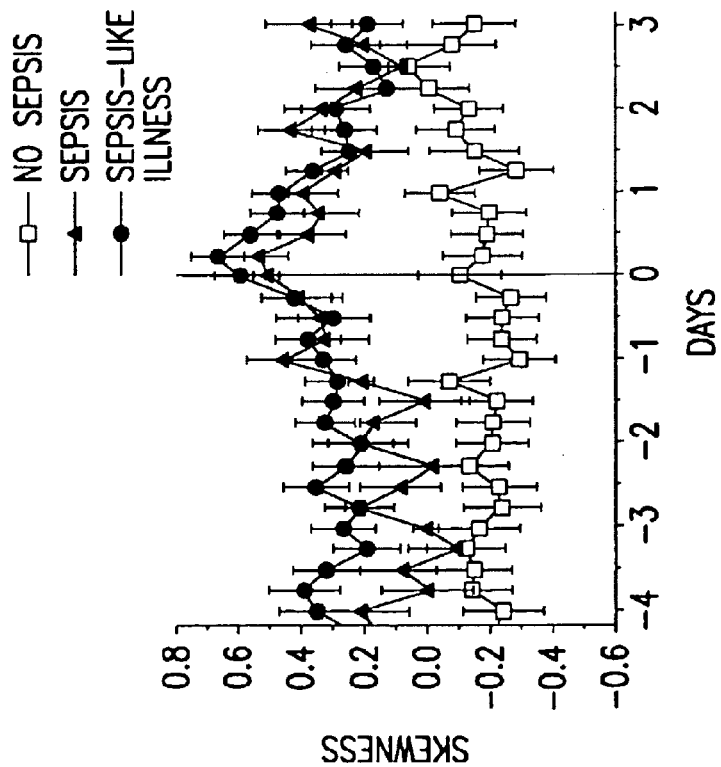

FIG. 1A shows a time series of 4096 RR intervals from an infant 6 days prior to an episode of culture-positive sepsis and represents a normal HR pattern. FIGS. 1B and 1C show abnormal RR interval time series from the same infant that were each obtained within 3 to 6 hours before sepsis was suspected and blood cultures were obtained. Both have a baseline of reduced variability and are punctuated by sharp upward deflections that represent short-lived episodes of HR decelerations. While episodes of bradycardia in NICU patients are common and not necessarily significant (Hodgman, J. E., T. Hoppenbrouwers, and L. A. Cabal, "Episodes of bradycardia during early infancy in the term-born and preterm infant," AJDC, 147:960–964 (1993)), frequent episodes of apnea, which are often associated with heart rate decelerations, are often interpreted as reflecting early stages of sepsis. Fanaroff, A. A., S. B. Korones, L. L. Wright, J. Verter, R. L. Poland, C. R. Bauer, J. E. Tyson, J. B. Philips, W. Edwards, J. F. Lucey, C. S. Catz, S. Shankaran, and W. Oh, "Incidence, presenting features, risk factors and significance of late onset septicemia in very low birth weight infants. The National Institute of Child Health and Human Development Neonatal Research Network," Pediatric Infectious Disease Journal, 17:593–598 (1998). The HR in these records always exceeded 120 beats per minute, and these episodes would have failed to trigger HR alarms set at usual thresholds of 100 beats per minute. In fact, the mean RR intervals of these records are not very different at 323 (1A), 308 (1B) and 302 msec (1C). Distinguishing the data in FIG. 1B from normal is nonetheless straightforward by calculating the standard deviation, here 11 msec compared with 32 msec for the normal. This measure, however, would fail to diagnose the abnormal time series in FIG. 1C where the episodes of sub-clinical HR decelerations are sufficient to elevate the standard deviation to an apparently normal value of 26 msec.

To diagnose these abnormalities, an approach was developed based on the frequency histograms of the RR intervals shown in the right-hand column in FIG. 1. The long RR intervals during the decelerations generated asymmetry of the histogram (1E and 1F). The symmetry of histograms was quantified using the third moment or skewness, a descriptive statistic that, like the standard deviation, is based on the differences between individual data points and the mean. The skewness is positive when there is a longer tail of values extending toward longer RR intervals. Weisstein, E. W., "CRC Concise Encyclopedia of Mathematics," Chapman and Hall/CRC, Boca Raton (1999). The skewness values of the three time-series are different: −0.12 for the data in 1A, indicating a near-symmetric distribution, but 1.99 and 1.33 for the data in FIGS. 1B and 1C, indicating a large degree of asymmetry.

The abnormalities of the histograms can also be quantified by considering the relationship of values in the distribution to the mean. Accordingly, the values of five percentile values of the normalized data—the 10th, 25th, 50th (median), 75th, and 90th was determined. These parameters differed among the three data sets shown. For example, the $_{50}$th percentile value (p50) was more negative in the abnormal data sets. The values were 0.13 in the normal record in FIG. 1A but −0.21 and −0.33 in the abnormal records shown in FIGS. 1B and 1C. This change results from the preponderance of values to the left of the center of the distribution, a consequence of the asymmetry of the histogram.

Summary HRC Data

FIG. 2 shows the time course of HRC measures for the three patient groups. Each data point is the mean of the median values for 6 hours, and bars are S.E.M. The vertical line marks the time of the abrupt clinical deterioration for which blood cultures were obtained and antibiotics were started. The label "CRASH" stands for Cultures, Resuscitation and Antibiotics Started Here. The data points at time 0 represent the 6-hour epoch prior to, but not including, the time of the deterioration. Values of mean RR interval (2A) and standard deviation (2B) did not discriminate among the groups. The skewness (2C) and p50 values (2D), on the other hand, changed markedly in the epochs from 24 hours before to 24 hours after diagnosis. The skewness was 0.59±0.10 for the sepsis group and 0.51±0.12 for the sepsis-like illness group compared with −0.10±0.13 for control over the 6 hours prior to clinical suspicion. The values for sepsis (culture-positive) and sepsis-like illness (culture-negative) infants were not significantly different, but both were different than the control values (p<0.001). The p50 was −0.0298±0.014 for sepsis and −0.0223±0.015 for sepsis-like illness compared with +0.0503±0.016 for control over the 6 hours prior to clinical suspicion. Again, the values for sepsis and sepsis-like illness groups were not significantly different, but both were different than the control values (p<0.001).

Clinical Scores

Figure 3B:
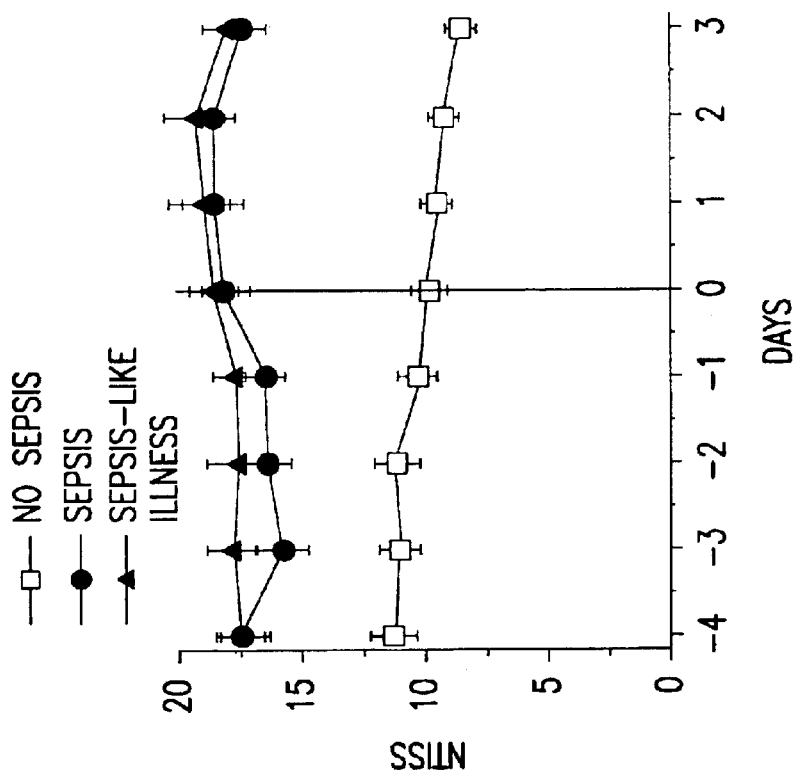
FIG. 3 illustrates a time course of clinical scores. Data points are the mean score over 24 hours; bars are standard error of the mean ("S.E.M"). Both SNAP and NTISS are higher in the sepsis and sepsis-like illness groups. In the 24 hours S.E.M.=standard error of the mean; SNAP=Score for Neonatal Acute Physiology; NTISS=Neonatal Therapeutic Intervention Scoring System; CRASH=Cultures, Resuscitation and Antibiotics Started Here.
Figure 3A:
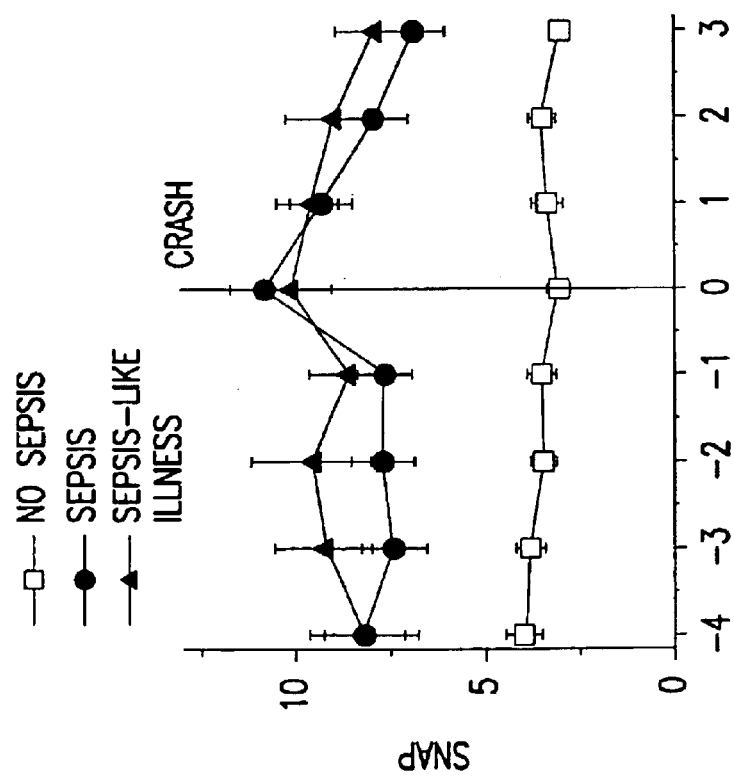

FIG. 3 shows the Score for Neonatal Acute Physiology (SNAP) and Neonatal Therapeutic Intervention Severity Score (NTISS) scores. The sepsis and sepsis-like illness groups had higher levels of both scores throughout, suggesting a greater degree of illness and intensity of interventions. The NTISS level declined over the 10 day period in the control group, consistent with declining requirement for therapies and gradual weaning from support systems. On day 0, the 24 hours prior to (but not including) the clinical suspicion of sepsis, SNAP rose further in the sepsis and sepsis-like illness groups (p=0.01, ANOVA) and there was no decline in NTISS. Over the 24 hours before and after the CRASH, the values of SNAP and NTISS for sepsis (culture-positive) and sepsis-like illness (culture-negative) infants were not significantly different, but both were different than the control values (p<0.001).

Multivariable Logistic Regression Analysis

Multivariable logistic regression analysis was performed on the data from the 24 hours prior to the clinical suspicion of sepsis. HRC were represented by the median values of each of the five percentiles, and clinical data were represented by both the SNAP and NTISS scores for this period. The data from the sepsis and sepsis-like illness groups were pooled. Whether a regression model could distinguish the pooled data from the control group was tested. The finding was that the groups were highly significantly different (p<0.0001, ROC area 0.9). While no single HR percentile measure made a significantly greater contribution than the others to the discriminatory ability of the model, SNAP contributed significantly more than NTISS (p<0.003, Wald z-test). Both HRC and clinical scores contributed independently to the final model (p=0.02). Results were similar when only sepsis or sepsis-like illness infants were analyzed, and for regression models using HR moments rather than percentiles.

Dynamic Changes in HRC and Illness Severity Scores Early in the Course of Sepsis ROC analysis was used to quantify differences among the groups, and to examine the time course of the differences. The area under the ROC plot is 0.5 when the groups are not different, and it is 1.0 when the groups are entirely distinct. Panels A and B of FIG. 4 show the results for HR moments and percentiles. For this analysis, the results after pooling data from the sepsis and sepsis-like groups are shown, but the results for either group individually were very similar. While mean and S.D. did not discriminate controls from sepsis and sepsis-like illness infants, skewness showed dynamic differences beginning 12 to 24 hours prior to the diagnosis. For example, there is a significant difference between the values of p50 measured in the sepsis groups 3 days prior to sepsis compared with values 6 to 12 hours prior (p<0.05). The difference then resolved over the two days after diagnosis and antibiotic therapy. Two of the HR percentiles, p10 and p50, showed a similar course. SNAP and NTISS also discriminated between the control group and the sepsis and sepsis-like illness groups, and SNAP showed an increasing difference for one to two days prior to the diagnosis. The increasing ROC area for NTISS is due to the failure of NTISS to decline in the sepsis and sepsis-like illness infants shown in FIG. 3B.

Figure 4B:
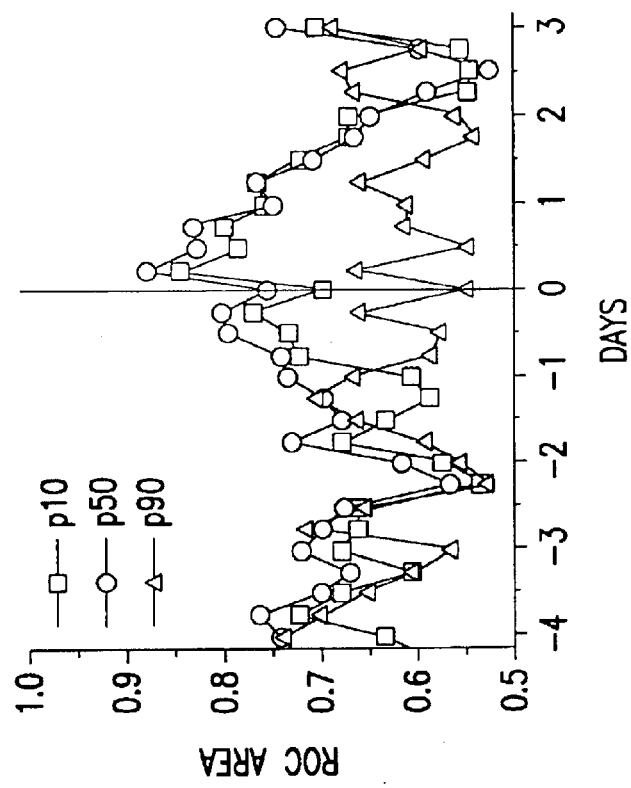
FIG. 4 illustrates a time course of Receiver Operating Characteristic ("ROC") areas. Panels A and B illustrate HRC measures. Panel C illustrates clinical scores and panel D illustrates regression models combining HRC and clinical scores. Abbreviation: S.D. is standard deviation; p10, p50 and p90 are the $10^{th}$, $50^{th}$, and $90^{th}$ percentile data points respectively; SNAP is Score for Neonatal Acute Physiology; NTISS is Neonatal Therapeutic Intervention Scoring System; CRASH is Cultures, Resuscitation and Antibiotics Started Here.
Figure 4A:
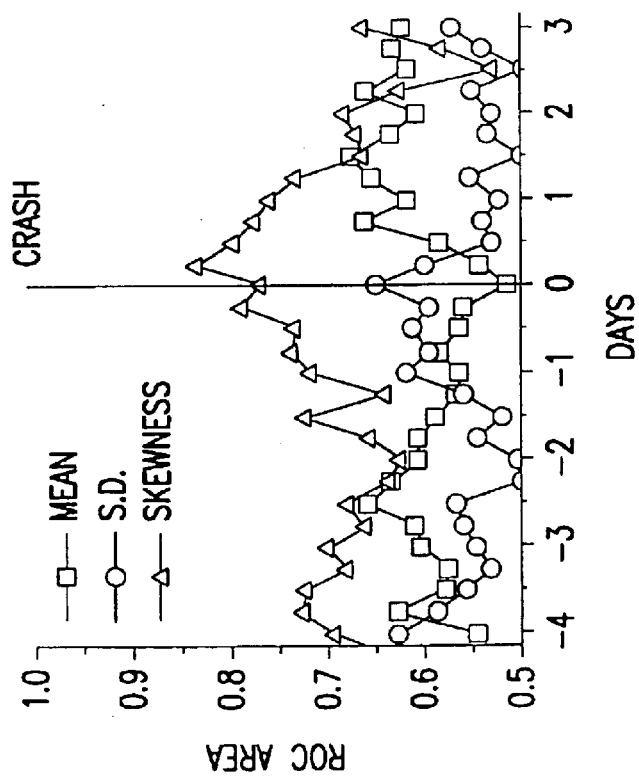
Figure 4D:
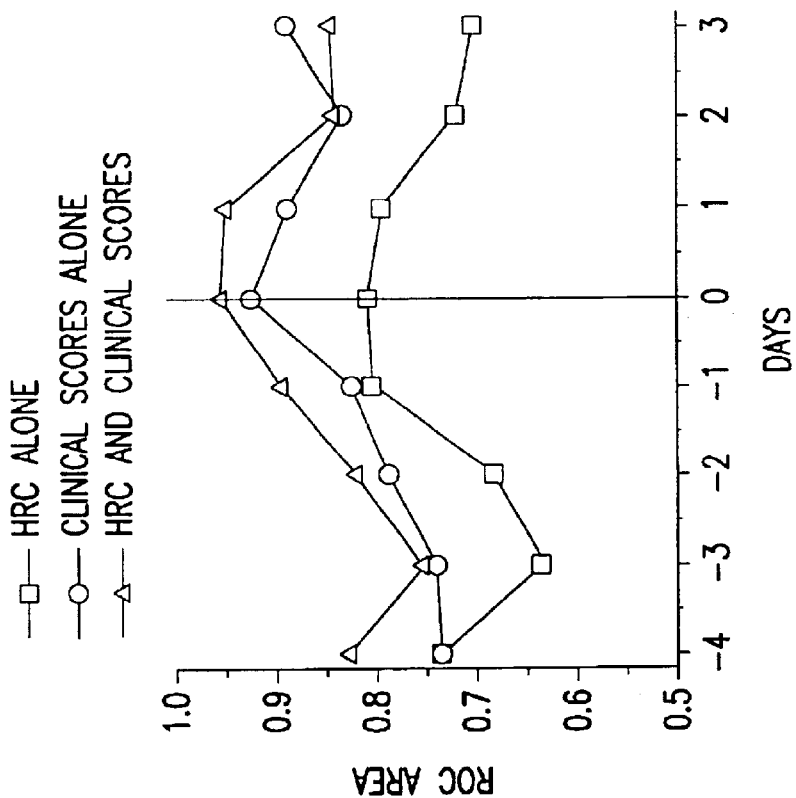
Figure 4C:
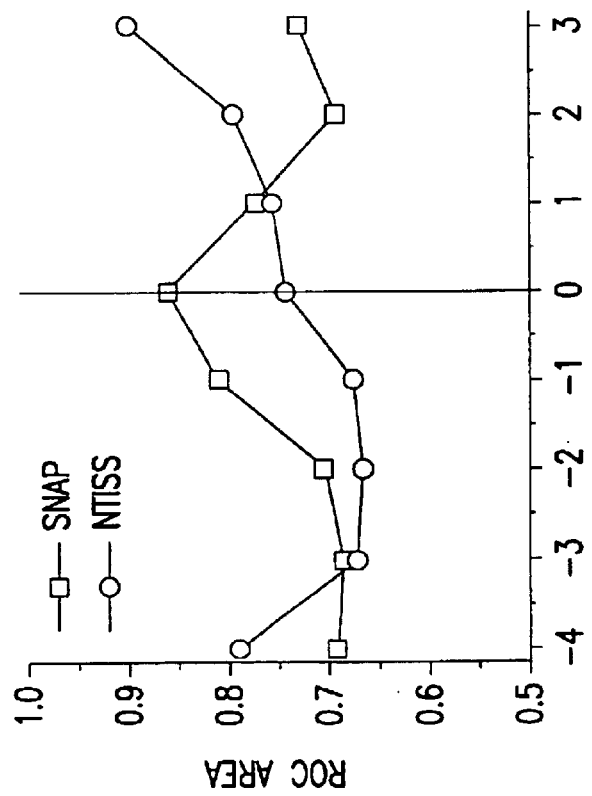
Figure 5:
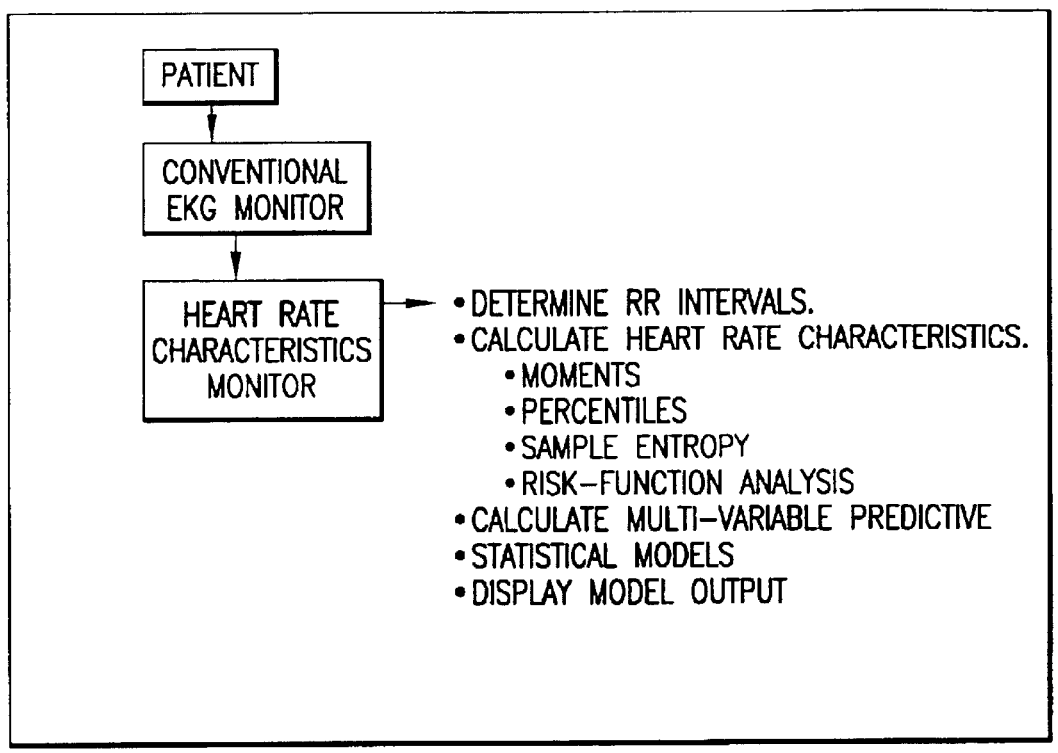
FIG. 5 is a schematic block diagram of an embodiment of the apparatus of the invention.

Multivariable logistic regression models were also used to distinguish the groups. As shown in FIG. 4D, models that used HRC alone and clinical scores (SNAP and NTISS together) alone effectively discriminated the groups, with larger changes at least one day prior to the diagnosis. A model using both HRC and clinical scores was superior, in keeping with the finding above that both HRC and clinical data contributed independently to the model. A comparison of regression model values for day −3 with subsequent days showed that the increases on day 0 were statistically significant for all models (p<0.05).

TABLE 1

Population Characteristics

| | No sepsis (n = 26/29) | Sepsis (n = 40/46) | Sepsis-like illness (n = 23/27) |
|---|---|---|---|
| Birth weight, g | | | |
| <750 | 3 | 20 | 12 |
| 750–999 | 12 | 14 | 8 |
| 1000–1499 | 10 | 5 | 2 |
| ≧1500 | 1 | 1 | 1 |
| Gestational age, wk | | | |
| <26 | 6 | 19 | 9 |
| 26–28 | 10 | 16 | 9 |
| 29–32 | 9 | 4 | 5 |
| >32 | 1 | 1 | 0 |
| Post-conceptional age at event, wk | | | |
| <26 | 0 | 1 | 4 |
| 26–28 | 0 | 13 | 7 |
| 29–32 | 13 | 20 | 8 |
| >32 | 16 | 12 | 8 |
| Male sex | 15 | 21 | 13 |
| Caucasian | 21 | 30 | 21 |

KEY: Data are the number of patients for birth weight and gestational age, and numbers of episodes for post-conceptional age at event. In the column headings the totals are given as (n = number of patients, number of episodes).

Example 2

149 consecutive patients in the University of Virginia (UVA) NICU were studied. There were 110 episodes of sepsis (positive blood culture) and sepsis-like illness (no proven infection) in 69 patients. A repeated measures multivariable logistic regression model using parameters of sample entropy, sample asymmetry analysis and standard deviation showed highly significant association with impending sepsis and sepsis-like illness (ROC area 0.71, p<0.001). The results were the same for different values of m and r in the SampEn calculation, and for several parameters from the sample asymmetry analysis including left-risk, right risk, and the two measures in combination, such as their ratio. Similar results were obtained using k-nearest neighbor analysis, another multivariable statistical technique, to combine these HRC measures. HRC added significantly to the predictive information of birth weight (BW), gestational age (GA), and days of age (p<0.001, Wald test). A full model using BW, GA, days of age and HRC had ROC area 0.75 (95% confidence interval 0.68 to 0.76). The potential clinical usefulness of these findings was evaluated using a threshold-independent approach: A change in the HRC index from the $25^{th}$ percentile to the 75th percentile increased the odds of sepsis or sepsis-like illness by 4.5-fold.

Example 3

197 patients in the Wake Forest University NICU were studied using the method set forth in Example 4. There were 71 episodes of sepsis and sepsis-like illness in 60 of the 197 infants. The predictive model that was developed at UVA showed highly significant association with impending sepsis and sepsis-like illness (ROC area 0.71, p<0.001). Again, HRC added significantly to the predictive information of BW, GA, and days of age (p<0.001, Wald test). A change in the HRC index from the $25^{th}$ percentile to the $75^{th}$ percentile increased the odds of sepsis or sepsis-like illness by 4.2-fold, which illustrate that HRC monitoring is a valid and useful non-invasive tool in the early diagnosis of sepsis and sepsis-like illness.

We claim:

1. A method for early detection of subacute, potentially catastrophic illness in a patient comprising:
    (a) monitoring the patient's frequency histograms of RR, intervals;
    (b) generating a data set of the frequency histograms of RR intervals;
    (c) calculating one or more of
        (i) moments of the data set selected from the second and higher moments, including standard deviation
        (ii) percentile values of the data set,
        (iii) sample entropy, and
        (iv) sample asymmetry,
    (d) identifying an abnormal heart rate variability associated with the illness based on one or more of the moments and the percentile values, the sample entropy and the sample asymmetiy analysis.

2. The method of claim 1, wherein the moments include the second moment of the data set.

3. The method of claim 1, wherein the moments include the third moment and the standard deviation of the data set.

4. The method of claim 1, wherein the moments include the fourth moment of the data set.

5. The method of claim 1, wherein the percentile values include about the 10th and/or $50^{th}$ percentile value.

6. The method of claim 1, wherein the sample entropy is calculated.

7. The method of claim 1, wherein the sample asymmetry is calculated.

8. The method of claim 1 wherein step (c) is carried out using a multivariable statistical analysis selected from the group consisting of but not limited to multivariable regression analysis, neural networks, k-nearest neighbor analysis, and combinations thereof.

9. The method of claim 8 wherein the multivariable statistical analysis is multivariable regression analysis.

10. The method of claim 8 wherein the multivariable statistical analysis is a neural network.

11. The method of claim 8 wherein the multivariable statistical analysis is k-nearest neighbor analysis.

12. The method of claim 8 wherein the patient is a neonate.

13. The method of claim 8 wherein the patient is an infant.

14. The method of claim 8 wherein the patient is a toddler.

15. The method of claim 8 wherein the patient is a child.

16. An apparatus for early detection of subacute, potentially catastrophic infectious illness in a patient comprising (1) a monitoring device, which monitors the patient's frequency histograms of RR intervals, and (2) a microprocessor, said microprocessor performing steps comprising:
   (a) generating a data set of the frequency histograms of RR intervals;
   (b) calculating one or more of
      (i) moments of the data set selected from the second and higher moments,
      (ii) percentile values of the data set,
      (iii) sample entropy, and
      (iv) sample asymmetry,
   (c) identifying an abnormal heart rate variability associated with the illness based on one or more of the moments, the percentile values, the sample entropy and the sample asymmetry analysis.

17. The apparatus of claim 16, wherein the microprocessor calculates the second moment of the data set.

18. The apparatus of claim 16, wherein the microprocessor calculates the third moment of the data set.

19. The apparatus of claim 16, wherein the microprocessor calculates the fourth moment of the data set.

20. The apparatus of claim 16, wherein the microprocessor calculates the $10^{th}$ and/or $50^{th}$ percentile of the data set.

21. The apparatus of claim 16, wherein the microprocessor calculates the sample entropy.

22. The apparatus of claim 16, wherein the microprocessor calculates sample asymmetry of the data set.

23. The application of claim 16, wherein the microprocessor performs step (b) by carrying Out using a multivariable statatistical analysis selected from the group including but not limited to multivariable regression analysis, neural networks, k-nearest neighbor analysis, and combinations thereof, k-nearest neighbor analysis, neural networks, or combination thereof.

\* \* \* \* \*